(12) United States Patent
Williams et al.

(10) Patent No.: US 7,189,688 B2
(45) Date of Patent: Mar. 13, 2007

(54) PERFUMING INGREDIENT WITH A FLORAL CHARACTER

(75) Inventors: Alvin Scott Williams, Nyon (CH); Charles Fehr, Versoix (CH)

(73) Assignee: Firmenich SA, Geneva (CH)

( * ) Notice: Subject to any disclaimer, the term of this patent is extended or adjusted under 35 U.S.C. 154(b) by 586 days.

(21) Appl. No.: 10/781,134

(22) Filed: Feb. 17, 2004

(65) Prior Publication Data

US 2004/0167059 A1   Aug. 26, 2004

(30) Foreign Application Priority Data

Feb. 24, 1920   (WO) .................. PCT/IB03/00650

(51) Int. Cl.
*A61Q 13/00*   (2006.01)
(52) U.S. Cl. .............. 512/25; 512/8; 512/11; 512/26; 560/126; 549/512; 549/554
(58) Field of Classification Search ............ 512/8, 512/11, 25, 26; 560/126; 549/512, 554
See application file for complete search history.

(56) References Cited

U.S. PATENT DOCUMENTS 5,767,305 A * 6/1998 Monteleone et al. ....... 560/124

6,051,548 A * 4/2000 Boden et al. .................. 512/22

FOREIGN PATENT DOCUMENTS

| DE | 19 23 223 A | 11/1969 |
|---|---|---|
| EP | 1 318 144 A1 | 6/2003 |
| WO | WO 00/14051 | 3/2000 |

* cited by examiner

*Primary Examiner*—Monique T. Cole
(74) *Attorney, Agent, or Firm*—Winston & Strawn LLP

(57) ABSTRACT

The present invention concerns a compound or mixtures of compounds of formula

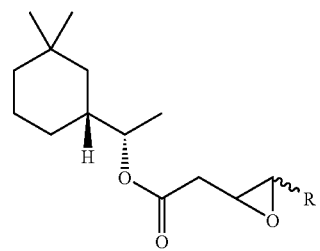

(I)

wherein R represents a linear, branched or cyclic $C_{1-3}$ hydrocarbon group, and the wavy line indicates that the substituents on the epoxide moiety may have a cis or trans configuration. One or more of these compounds can be used as perfuming ingredients.

10 Claims, No Drawings

PERFUMING INGREDIENT WITH A FLORAL CHARACTER

BACKGROUND

The invention concerns the perfumery industry and in particular perfuming ingredients which are esters of some of epoxy-carboxylate compounds. The compounds of the invention are believed to be new. Indeed, the closest analogues reported in the literature, in terms of chemical structure, are the compounds disclosed in WO 00/14051. However, those analogues not only have a different chemical structure, i.e., a ketone group instead of an epoxide moiety, but also possess organoleptic properties which are significantly different from those of the compounds according to the present invention.

SUMMARY OF THE INVENTION

The present invention concerns a compound of formula

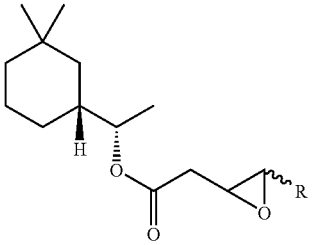

(I)

wherein R represents a linear, branched or cyclic C1–3 hydrocarbon group, and the wavy line indicates that the substituents on the epoxide moiety may have a cis or trans configuration. The compounds of formula (I), or a mixture thereof, may advantageously be used as perfuming ingredients. The invention also concerns the compositions or the articles comprising as active ingredient at least a compound of formula (I).

DETAILED DESCRIPTION OF THE PREFERRED EMBODIMENTS

Surprisingly, we have now established that a compound of formula

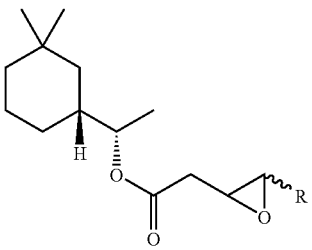

(I)

wherein R represents a linear, branched or cyclic $C_{1-3}$ hydrocarbon group, and the wavy line indicates that the substituents on the epoxide moiety may have a cis or trans configuration, or a mixture of compounds of formula (I), possesses surprising odor properties, of the fruity type, which have been found to be particularly useful and appreciated for the preparation of perfumes, perfuming compositions and perfumed products.

According to a particular embodiment of the invention, a compound of formula (I) wherein R is an ethyl group has proved to be a remarkably useful perfuming ingredient. For instance, (1S,1'R)-1-(3',3'-dimethyl-1'-cyclohexyl)ethyl trans-3,4-epoxyhexanoate is much appreciated by perfumers for its fruity odor. Indeed, the odor has a pronounced fruity character associated with a musky and slightly animal connotation or aspect. The fruity character, which is of the pear and prune type with a berry bottom note, has a remarkable persistence and is still clearly perceivable in the bottom notes. Such persistence is quite rare for this kind of ester-fruity note.

The overall fragrance of this compound is remarkably more fruity and powdery, and consequently much less musky, than the known analogues cited above. The invention's compounds provide therefore a very interesting new tool to the perfumer's palette.

(1S,1'R)-1-(3',3'-dimethyl-1'-cyclohexyl)ethyl cis-3,4-epoxyhexanoate possesses a more fruity and even less musky odor than the one of the trans isomer cited above. Moreover the odor of the cis isomer is slightly less pronounced than the one of the trans isomer, making the latter a preferred embodiment of the invention.

Another example of invention's compound is the (1S, 1'R)-1-(3',3'-dimethyl-1'-cyclohexyl)ethyl trans-3,4-epoxypentanoate which displays fruity odor notes, of the red fruit type, and a musky character as for the trans-3,4-epoxyhexanoate cited above. However the overall odor of the trans-3,4-epoxypentanoate is weaker than the one of the trans-3,4-epoxyhexanoate derivative.

Moreover, due to the surprising properties of the compounds of formula (I), another embodiment of the present invention is a perfuming composition comprising i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. The carrier may be a liquid or a solid.

As liquid carrier one may cite, as non-limiting examples, an emulsifying system, i.e., a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. As solid carrier one may cite, as non-limiting examples, absorbing gums or polymers, or yet an encapsulating materials. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient. Such a perfuming co-ingredient is not of the formula (I).

Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability and etceteras. A detailed description of the nature and type of adjuvant commonly used in perfuming bases cannot be exhaustive, but it has to be mentioned that the ingredients are well known to a person skilled in the art.

An inventive composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the invention compound can also be advantageously used in all the fields of modern perfumery to positively impart or modify the odor of a consumer product into which the compound (I) is added. Consequently, a perfumed article comprising:

i) as perfuming ingredient, at least one compound of formula (I) or an invention's perfuming composition; and ii) a consumer product base is also a feature of the present invention.

For the sake of clarity, it has to be mentioned that, by "consumer product base" we mean here a consumer product which can be associated with a perfuming composition, i.e. a consumable product such as a detergent or a perfume. In other words, a perfumed article according to the invention comprises the functional formulation, as well as optionally additional benefit agents, corresponding to a desired consumer product, e.g. a detergent or an air freshener, and an olfactive effective amount of at least one inventive compound.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which a compound of formula (I) can be incorporated into the various aforementioned articles or compositions vary within a wide range of values. These values are dependent on the nature of the article or product to be perfumed and on the olfactory effect desired as well as on the nature of the co-ingredients in a given composition when the compounds according to the invention are mixed with perfuming co-ingredients, solvents or additives commonly used in the art.

For example, typical concentrations from 1% to 20%, and preferably from 5% to 15%, by weight of this compound, with respect to the perfuming composition in which they are incorporated, can be typically used. Lower concentrations than these can be used when the invention's compound is directly applied for perfuming some of the consumer products mentioned above.

As mentioned above, the invention concerns the use of a compound of formula (I) as perfuming ingredients. In other words it concerns a method to confer, enhance, improve or modify the odor properties of a perfuming composition or of a perfumed article, which method comprise adding to the composition or article an effective amount of at least a compound of formula (I). By "use of a compound of formula (I)" it has to be understood here also the use of one of the inventive composition.

EXAMPLES

The invention will now be described in further detail by way of the following examples, wherein the temperatures are indicated in degrees centigrade (° C.); the NMR spectral data were recorded with a 400 MHz machine in $CDCl_3$; the chemical displacements δ are indicated in ppm with respect to the TMS as standard and all the abbreviations have the usual meaning in the art.

Example 1

Synthesis of (1S,1'R)-1-(3',3'-dimethyl-1'-cyclohexyl)ethyl trans-3,4-epoxyhexanoate a) A solution of (−)-(1R,1'S)-1-(3',3'-dimethyl-1'-cyclohexyl)-1-ethanol (13.88 g, 89 mmol), (E)-3-hexenoic acid (10.14 g, 89 mmol) and para-toluenesulfonic acid (0.14 g) in toluene (120 ml) was heated to reflux for 20 hours. The mixture was then cooled to room temperature washed with $NaHCO_3$ (sol.), water and concentrated. The remaining oil was distilled (Vigreux 20 cm) to give (1S,1'R)-1-(3',3'-dimethyl-1'-cyclohexyl)ethyl (E)-3-hexenoate (15.84 g, 70% yield, 99.9% GC).

B.P. 62.5° C./53 Pa

MS:139 (36), 123 (36), 114 (77), 109 (15), 97 (36), 83 (100), 69 (88), 55 (30), 41 (28).

$^{13}$C-NMR:171.9 (s), 136.1 (d), 121.0 (d), 74.8 (d), 41.3 (t), 39.1 (t), 38.5 (t), 38.4 (d), 33.5 (q), 30.5 (s), 28.4 (t), 25.5 (t), 24.6 (q), 22.0 (t), 17.2 (q), 13.5 (q).

$^{1}$H-NMR:0.80–1.70 (m, 9H without Me-signals), 0.87 (s, 3H), 0.90 (s, 3H), 1.00 (t, J=7, 3H), 1.15 (d, J=6, 3H), 2.05 (quint, J=7, 2H), 3.00 (d, J=6, 2H), 4.69 (quint, J=6, 1H), 5.57 (m, 2H).

b) Water containing 70% meta-chloroperbenzoic acid (mCPBA) (21.3 g; 86.4 mmol) in $CH_2Cl_2$ (70 ml) was added in 20 minutes to a stirred emulsion of (1S,1'R)-1-(3',3'-dimethyl-1'-cyclohexyl)ethyl (E)-3-hexenoate (17.5 g; 68.4 mmol), $CH_2Cl_2$ (180 ml) and $NaHCO_3$ (8.70 g; 103.7 mmol) in water (100 ml) kept at 15–20° C. The mixture was stirred at room temperature for 15 hours. The phases were separated and the aqueous phase was extracted with $Et_2O$. The organic layer was washed (10% aqueous $Na_2SO_3$, $H_2O$, then brine), dried ($Na_2SO_4$), evaporated and distilled over $CaCO_3$ (200 mg) to collect a fraction boiling at 165° C./0.05 mbars. This fraction was further purified by a mild bulb-to-bulb distillation (oven temp. 70° C./0.01 mbars) of the volatile products in order to recover the residue, consisting essentially of pure title compound. The yield was 80%.

B.P. 110° C./40 Pa

MS:155 (9), 138 (77), 130 (36), 123 (99), 109 (64), 95 (60), 83 (93), 69 (100), 55 (49), 41 (37).

$^{13}$C-NMR:170.1 (s), 75.4 (d), 59.6 (d), 53.8 (d), 41.3 (t), 39.1 (t), 38.3 (d), 38.2 (t), 33.5 (q), 30.5 (s), 28.4 (t), 24.8 (t), 24.6 (q), 21.9 (t), 17.1 (q), 9.6 (q).

$^{1}$H-NMR:0.80–1.70 (m, 11H without Me-signals), 0.88 (s, 3H), 0.91 (s, 3H), 1.01 (t, J=7, 3H), 1.18 (d, J=6, 3H), 2.46 (m, 1H), 2.63 (m, 1H), 2.74 (m, 1H), 3.05 (m, 1H), 4.75 (m, 1H).

Example 2

Synthesis of (1S,1'R)-1-(3',3'-dimethyl-1'-cyclohexyl)ethyl cis-3,4-epoxyhexanoate a) Using the same experimental procedure than in Example 1.a), but with (Z)-3-hexenoic acid, instead of the (E) isomer, (1S,1'R)-1-(3',3'-dimethyl-1'-cyclohexyl)ethyl (Z)-3-hexenoate was obtained with a yield of 88%.

MS:139 (37), 123 (21), 114 (36), 97 (30), 83 (100), 69 (95), 55 (40), 41 (50).

$^{13}$C-NMR:171.7 (s), 134.9 (d), 120.5 (d), 74.9 (d), 41.3 (t), 39.1 (t), 38.4 (t), 33.5 (d), 33.3 (t), 30.5 (s), 28.4 (t), 24.6 (q), 22.0 (t), 20.7 (t), 17.1 (q), 14.0 (q).

$^{1}$H-NMR:0.80–1.70 (m, 9H without Me-signals), 0.87 (s, 3H), 0.91 (s, 3H), 0.98 (t, J=7, 3H), 1.26 (d, J=6, 3H), 2.07 (quint, J=7, 2H), 3.06 (d, J=6, 2H), 4.70 (quint, J=6, 1H), 5.55 (m, 2H).

b) Water containing 70% meta-chloroperbenzoic acid (mCPBA) (21.3 g; 86.4 mmol) in $CH_2Cl_2$ (70 ml) was added in 20 minutes to a stirred emulsion of (1S,1'R)-1-(3',3'-dimethyl-1'-cyclohexyl)ethyl (Z)-3-hexenoate (17.5 g; 68.4 mmol), $CH_2Cl_2$ (180 ml) and $NaHCO_3$ (8.70 g; 103.7 mmol) in water (100 ml) kept at 15–20° C. The mixture was stirred at room temperature for 15 hours. The phases were separated and the aqueous phase was extracted with $Et_2O$. The organic layer was washed (10% aqueous $Na_2SO_3$, $H_2O$, then brine), dried ($Na_2SO_4$), evaporated and distilled over $CaCO_3$ (200 mg) at 100–120° C./0.01 mbars. The title compound was thus obtained with a yield of 98%.

MS:155 (4), 138 (44), 130 (36), 123 (63), 113 (31), 109 (40), 95 (43), 83 (79), 71 (61), 69 (100), 55 (58), 41 (64).

$^{13}$C-NMR:170.3 (s), 75.4 (d), 57.7 (d), 52.7 (d), 41.3 (t), 39.1 (t), 38.3 (d), 34.0 (t), 33.5 (q), 30.5 (s), 28.3 (t), 24.6 (q), 21.9 (t), 21.2 (t), 17.1 (q), 10.5 (q).

$^{1}$H-NMR:0.80–1.70 (m, 11H without Me-signals), 0.87 (s, 3H), 0.91 (s, 3H), 1.05 (t, J=7, 3H), 1.18 (d, J=6, 3H), 2.48 (m, 1H), 2.63 (m, 1H), 2.94 (m, 1H), 3.33 (m, 1H), 4.75 (m, 1H).

Example 3

Synthesis of (1S,1'R)-1-(3',3'-dimethyl-1'-cyclohexyl)ethyl trans-3,4-epoxypentanoate a) Using the same experimental procedure than in Example 1.a), but with (E)-3-pentenoic acid, instead of (E)-3-hexenoic acid, (1S,1'R)-1-(3',3'-dimethyl-1'-cyclohexyl)ethyl (Z)-3-pentenoate was obtained with a yield of 65%.

MS:139 (21), 123 (18), 100 (48), 83 (100), 69 (71), 55 (85).

$^{13}$C-NMR:171.9 (s); 129.1 (d); 123.1 (d); 74.9 (d); 41.3 (t); 39.1 (t); 38.4 (t); 38.4 (d); 33.5 (q); 30.5 (s); 28.4 (t); 24.6 (q); 22.0 (t); 17.9 (q); 17.2 (q).

$^{1}$H-NMR:0.80–1.70 (m, 9H without Me-signals), 0.86 (s, 3H), 0.90 (s, 3H), 1.25 (d, J=6, 3H); 1.70 (m, 3H); 2.99 (m, 2H); 4.68 (quint, J=6, 1H); 5.55 (m, 2H).

b) Using the same experimental procedure than in Example 1.b), the desired epoxypentanoate was obtained with a yield of 56%.

MS:155 (4), 138 (41), 123 (67), 109 (47), 99 (62), 95 (48), 83 (61), 69 (100), 55 (85), 43 (77).

$^{13}$C-NMR:171.1 (s); 75.4 (d); 55.1 (d); 54.5 (d); 41.3 (t); 39.1 (t); 38.3 (d); 38.1 (t); 33.5 (q); 30.5 (s); 28.3 (t); 24.6 (q); 21.8 (t); 17.3 (q); 17.1 (q).

¹H-NMR:0.80–1.70 (m, 9H without Me-signals), 0.87 (s, 3H), 0.91 (s, 3H), 1.18 (d, J=7, 3H); 1.34 (m, 3H); 2.48 (m, 1H); 2.61 (m, 1H); 2.84 (m, 1H); 3.01 (m, 1H); 4.74 (m, 1H).

Example 4

Preparation of a Perfuming Composition

A perfume base composition of the "musky" type was prepared by admixing the following ingredients:

| Ingredient | Parts by weight |
| --- | --- |
| Ambrette[1] synth. | 1 |
| Exaltolide ®[2] Total | 22 |
| Helvetolide ®[3] | 25 |
| 0.1%* Perhydro-4α,8aβ-dimethyl-4a-naphthalenol | 2 |
| Total | 50 |

*in dipropyleneglycol
[1] Compounded perfumery base; origin: Firmenich SA, Geneva, Switzerland
[2] 15-Pentadecanolide; origin: Firmenich SA, Geneva, Switzerland
[3] (+)-(1S,1'R)-2-[1-(3',3'-dimethyl-1'-cyclohexyl)ethoxy]-2-methylpropyl propanoate; origin: Firmenich SA, Geneva, Switzerland The addition of 50 parts by weight of (1S,1'R)-1-(3',3'-dimethyl-1'-cyclohexyl)ethyl trans-3,4-epoxyhexanoate to the above-described perfume base provided to the latter a pronounced fruity-waxy, pear-prune character, which was quite persistent. When, instead of the invention compounds there was added to the perfume base mentioned above the same amount of the known musk Romandolide®, i.e. (1S, 1'R)-[1-(3',3'-dimethyl-1'-cyclohexyl)ethoxycarbonyl]methyl propanoate (WO 00/14501, origin: Firmenich SA), then the olfactive effect obtained was much more musky, of the Galaxolide® type (1,3,4,6,7,8-hexahydro-4,6,6,7,8,8-hexamethyl-cyclopenta[g]isochromene, origin: IFF).

Example 5

Preparation of a Perfuming Composition

A perfuming composition of the "floral-fruity-violet" type was prepared by admixing the following ingredients:

| Ingredient | Parts by weight |
| --- | --- |
| Aldehyde C10 | 5 |
| Aldehyde C12 | 10 |
| 2-Methyl-undecenal | 20 |
| Methyl anthranilate | 5 |
| 4-Phenyl-2-butanone | 20 |
| Cetalox ®[1] | 10 |
| Citronellol | 50 |
| 4-Cyclohexyl-2-methyl-2-butanol[2] | 100 |
| Alpha Damascone | 5 |
| Dihydromyrcenol | 100 |
| Geraniol | 20 |
| Iso E Super ®[3] | 80 |
| Lilial ®[4] | 50 |
| 10%* Neobutenone ®[5] | 10 |
| Trans-1-(2,2,6-trimethyl-1-cyclohexyl)-3-hexanol[2] | 10 |
| Rose oxide | 5 |
| Verdyl propionate[6] | 60 |

-continued

| Ingredient | Parts by weight |
| --- | --- |
| 10%* Romascone ®[7] | 10 |
| Hexyl salicylate | 150 |
| Verdox ®[8] | 120 |
| Violettine MIP[2] | 10 |
| Total | 850 |

*in dipropyleneglycol
[1] 8,12-Epoxy-13,14,15,16-tetranorlabdane; origin: Firmenich SA, Geneva, Switzerland
[2] origin: Firmenich SA, Geneva, Switzerland
[3] 1-(Octahydro-2,3,8,8-tetramethyl-2-naphtalenyl)-1-ethanone; origin: International Flavors & Fragrances, USA
[4] 3-(4-Tert-butylphenyl)-2-methylpropanal; origin: Givaudan-Roure SA, Vernier, Switzerland
[5] 1-(5,5-Dimethyl-1-cyclohexen-1-yl)-4-penten-1-one; origin: Firmenich SA, Geneva, Switzerland
[6] origin: Givaudan-Roure SA, Vernier, Switzerland
[7] Methyl 2,2-dimethyl-6-methylene-1-cyclohexanecarboxylate; origin: Firmenich SA, Geneva, Switzerland
[8] 2-Tert-butyl-1-cyclohexyl acetate; origin: International Flavors & Fragrances, USA The addition of 150 parts by weight of (1S,1'R)-1-(3',3'-dimethyl-1'-cyclohexyl)ethyl trans-3,4-epoxyhexanoate to the above-described composition imparted to the latter a very distinct and persistent fruity-sweet character, which a musky-raspberry undernote.

Example 6

Preparation of a Perfuming Composition

A woman's perfume of the "fruity-musky" type was prepared by admixing the following ingredients:

| Ingredient | Parts by weight |
| --- | --- |
| Geranyl acetate | 10 |
| Styrallyl acetate | 5 |
| Hexylcinnamic aldehyde | 40 |
| 10%* Star anise essential oil | 10 |
| Benzophenone | 5 |
| Bergamot essential oil | 170 |
| 10%* Ethyl (E)-2,4-dimethyl-2-pentenoate | 25 |
| Raspberry ketone | 10 |
| Citral | 10 |
| 4-Cyclohexyl-2-methyl-2-butanol[1] | 30 |
| Coumarine | 10 |
| 2-Pentyl-1-cyclopentol[1] | 10 |
| 2-Methyl-4-(2,2,3-trimethyl-3-cyclopenten-1-yl)-4-penten-1-ol[1] | 50 |
| Florol ®[2] | 20 |
| English Clove essential oil | 5 |
| Hedione ® HC[3] | 50 |
| 10%* 3-(1,3-Benzodioxol-5-yl)-2-methylpropanal | 30 |
| Heliotropine | 5 |
| 10%* Hivernal ®[4] | 10 |
| 10%* Indol | 10 |
| Iralia ®[5] | 10 |
| Lavandin Grosso | 80 |
| 10%* Spearmint essential oil | 10 |
| 1,1,3,3,5-Pentamethyl-4,6-dinitro indan | 200 |
| Patchouli | 10 |
| Orange essential oil | 60 |
| 3-(5,5,6-Trimethyl-bicyclo[2.2.1]hept-2-yl)-1-cyclohexanol | 300 |
| Sclareolate ®[6] | 80 |

-continued

| Ingredient | Parts by weight |
|---|---|
| Wardia ®[7] | 10 |
| 10%* Red thyme essential oil | 15 |
| Basil oil | 10 |
| Total | 1300 |

*in dipropyleneglycol
[1] origin: Firmenich SA, Geneva, Switzerland
[2] Tetrahydro-2-isobutyl-4-methyl-4(2H)-pyranol; origin: Firmenich SA, Geneva, Switzerland
[3] Methyl dihydrojasmonate; origin: Firmenich SA, Geneva, Switzerland
[4] Mixture of 3-(3,3-dimethyl-5-indanyl)propanal and 3-(1,1-dimethyl-5-indanyl)propanal; origin: Firmenich SA, Geneva, Switzerland
[5] Mixture of methylionone isomeres; origin: Firmenich SA, Geneva, Switzerland
[6] Propyl (S)-2-(1,1-dimethylpropoxy)propanoate; origin: Firmenich SA, Geneva, Switzerland
[7] Compounded perfumery base; origin: Firmenich SA, Geneva, Switzerland The addition of 220 parts by weight of (1S,1'R)-1-(3',3'-dimethyl-1'-cyclohexyl)ethyl trans-3,4-epoxyhexanoate to the above-described woman's perfume imparted to the latter a fruity-blackberry connotation, together with a powdery-musk note. It would be impossible to obtain such olfactive effect by the addition of Romandolide®.

What is claimed is:

1. A compound of formula

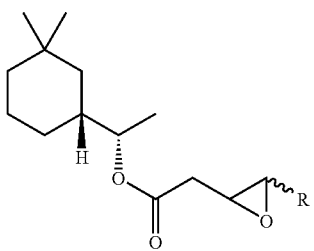

(I)

wherein R represents a linear, branched or cyclic $C_{1-3}$ hydrocarbon group, and the wavy line indicates that the substituents on the epoxide moiety may have a cis or trans configuration.

2. A compound according to claim 1, wherein R is an ethyl group.

3. As a compound according to claim 2, (1S,1'R)-1-(3',3'-dimethyl-1'-cyclohexyl)ethyl trans-3,4-epoxyhexanoate or (1S,1'R)-1-(3',3'-dimethyl-1'-cyclohexyl)ethyl cis-3,4-epoxyhexanoate.

4. A perfuming composition comprising:
    at least one compound of formula (I) as defined in claim 1; and
    at least one ingredient selected from the group consisting of a perfumery carrier and a perfumery base.

5. A perfuming composition according to claim 4, further comprising with at least one perfumery adjuvant.

6. A perfumed article comprising, as perfuming ingredient, at least one compound of formula (I), as defined in claim 1.

7. A perfumed article comprising, as perfuming ingredient, a perfuming composition as defined in claim 4.

8. A perfumed article according to claim 7, in the form of a solid or liquid detergent, a fabric softener, a perfume, a cologne or after-shave lotion, a perfumed soap, a shower or bath salt, mousse, oil or gel, a hygiene product or hair care product, a shampoo, a body-care product, a deodorant or antiperspirant, an air freshener, a cosmetic preparation, a fabric refresher, an ironing water, papers, wipes or bleaches.

9. A method to confer, enhance, improve or modify the odor properties of a perfuming composition or of a perfumed article, which method comprise adding to the composition or article an effective amount of at least one compound of formula (I), as defined in claim 1, perfuming composition as defined in claim 4.

10. A method to confer, enhance, improve or modify the odor properties of a perfuming composition or of a perfumed article, which method comprise adding to the composition or article an effective amount of a perfuming composition as defined in claim 4.

* * * * *

UNITED STATES PATENT AND TRADEMARK OFFICE
CERTIFICATE OF CORRECTION

PATENT NO.        : 7,189,688 B2                                            Page 1 of 1
APPLICATION NO.   : 10/781134
DATED             : March 13, 2007
INVENTOR(S)       : Williams et al.

It is certified that error appears in the above-identified patent and that said Letters Patent is hereby corrected as shown below:

<u>Title Page</u>:
Item (30) Foreign Application Priority Data, after "Feb. 24," delete "1920" and insert -- 2003 --.

<u>Column 10</u>:
Lines 35-36 (claim 9, lines 5-6), after "formula (I), as defined in claim 1" delete ", perfuming composition as defined in claim 4".

Signed and Sealed this

Seventh Day of August, 2007

JON W. DUDAS
*Director of the United States Patent and Trademark Office*